United States Patent [19]

Phillips

[11] 4,199,543
[45] Apr. 22, 1980

[54] TESTING APPARATUS FOR DISPENSING A FLUID

[76] Inventor: Robert E. Phillips, 12217 Iredell St., Studio City, Calif. 91604

[21] Appl. No.: 942,333

[22] Filed: Sep. 14, 1978

[51] Int. Cl.² ........................... G01N 1/10; G01N 1/14
[52] U.S. Cl. ..................................... 422/63; 422/103; 73/421 R; 73/425.6; 141/130
[58] Field of Search ................... 422/63, 66, 100, 103, 422/61; 73/421 R, 425.4, 425.6; 141/130

[56] References Cited

U.S. PATENT DOCUMENTS

| | | | |
|---|---|---|---|
| Re. 28,339 | 2/1975 | Maxon | 422/66 |
| 3,430,415 | 3/1969 | Phillips | 73/421 R |
| 3,791,509 | 2/1974 | Jones | 422/66 |

Primary Examiner—R. E. Serwin
Attorney, Agent, or Firm—Edward D. O'Brian

[57] ABSTRACT

A testing apparatus in which a vacuum holder mounted on a carrier is used to hold a specimen on the carrier as the carrier is moved from a first location to another location where the specimen is deposited can be modified so that the vacuum supplied to the vacuum holder is used to actuate a pump so as to dispense a predetermined quantity of fluid each time the carrier is in such another location. Such a modified apparatus can be utilized in medical testing in dispensing a reagent into an appropriate receptacle such as a test tube serving as a receiving means for the specimen. Such a structure is advantageous because it utilizes a single vacuum source for both holding a specimen on a carrier and for dispensing a liquid.

1 Claim, 1 Drawing Figure

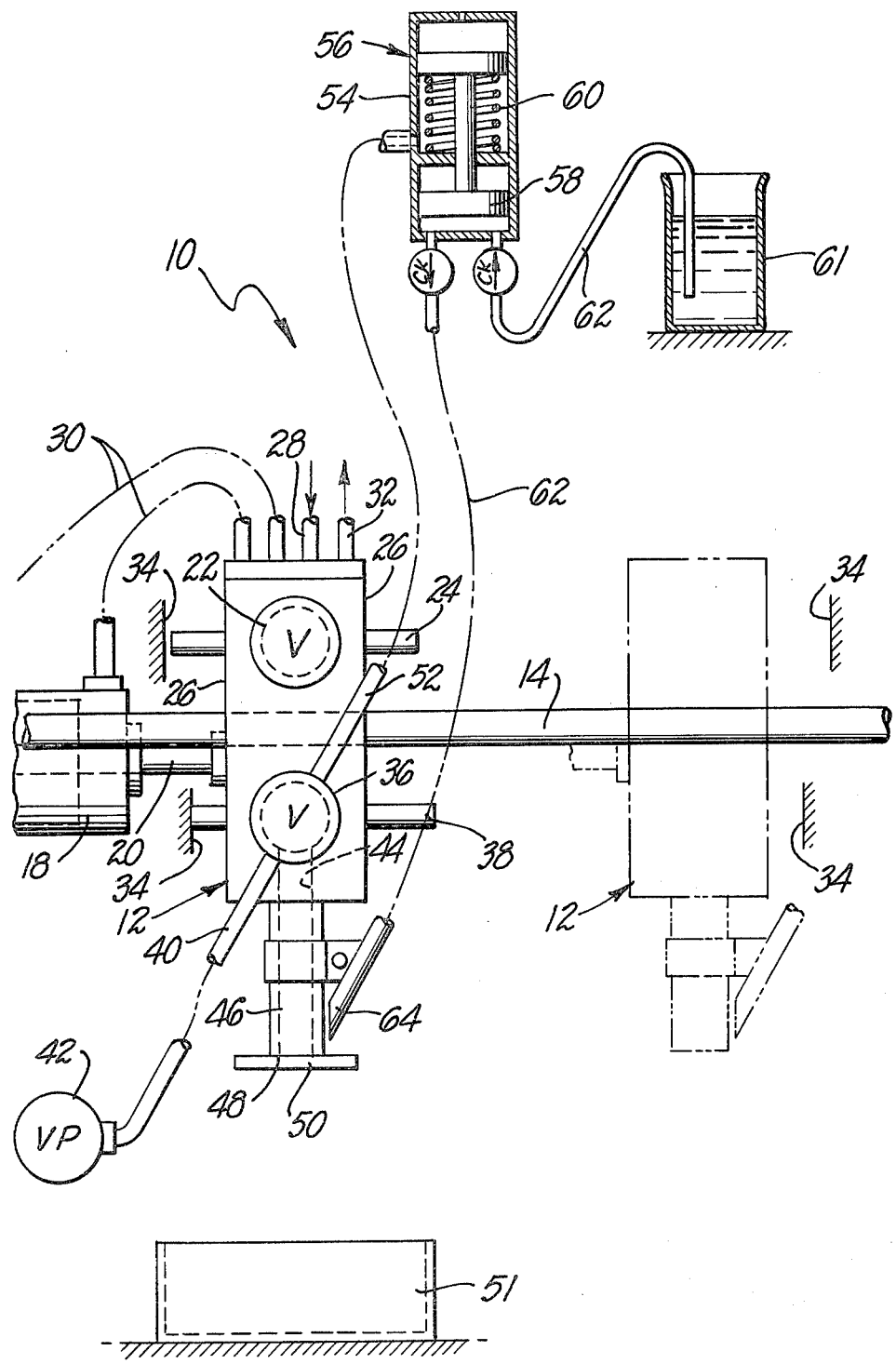

TESTING APPARATUS FOR DISPENSING A FLUID

BACKGROUND OF THE INVENTION

The invention set forth in this specification pertains to a new and improved testing apparatus. More specifically it pertains to a testing apparatus which is utilized to both move a specimen from one location to another and to dispense a quantity of a solution at such a second location.

At the present time testing apparatuses or devices are widely known which are used to remove a specimen from a sample and to transport such a specimen on a carrier away from the sample to a location adjacent to a receiving means and which are constructed so as to deposit such a specimen in or on such a receiving means. Structures of this type are commonly utilized in conducting a variety of different tests. Although such devices may be constructed in a variety of different manners, it is presently considered preferable to construct such devices as indicated in the Phillips U.S. Pat. No. 3,430,415, issued Mar. 4, 1969, entitled "TESTING DEVICE".

Although testing apparatuses as indicated in the preceding are considered to be quite desirable, in the past the utility of such testing devices has been limited to a degree because of the fact that such devices were not constructed so as to dispense a quantity of a liquid, such as a reagent, into a receptacle or test tube as indicated in the preceding more or less concurrently with the location of a specimen in such a container. Obviously there are various ways that this limitation of such prior testing devices could be overcome.

Thus, for example, it is possible to move receptacles or test tubes indicated in the preceding directly beneath an appropriate dispensing structure for dispensing a predetermined quantity of a solution into such a container. This is considered undesirable because it involves the use of a secondary piece of equipment other than a basic testing device as briefly indicated in the preceding discussion. The simple expedient of locating a reagent or the like into a container as noted by hand is considered undesirable because of the time involved and because of the possibility of human error.

SUMMARY OF THE INVENTION

As a result of the various factors indicated in the preceding it is considered that there is a need for new and improved testing devices or testing apparatuses which are constructed so as to be capable of being used in transporting a specimen from a first location to another location and which are capable of depositing a predetermined quantity of solution along with the specimen to such another location. A broad objective of the present invention is to fulfill this need. Other objectives of the invention are to provide testing apparatuses as indicated which are comparatively inexpensive to construct when the costs of their construction are compared with the costs of constructing known testing devices, which are desirable from a utilitarian standpoint, and which are extremely reliable in performance and operation.

In accordance with this invention these various objectives are achieved by providing in a testing apparatus which includes a carrier for use in transporting a specimen from a first location to another location, means for moving the carrier from the first location to the other location and back to the first, a vacuum source, a vacuum holding means for holding the specimen on the carrier through the use of a vacuum, a line connecting the vacuum source with the holding means, the line including a valve, and control means for operating the valve so that a vacuum is supplied to the holding means when the carrier is in the first location and as the carrier is moved to the other location and is not supplied to the holding means when the holding means is located at the other location in which the improvement comprises: a pump means for pumping a predetermined quantity of a solution each time the pump means is actuated; a vacuum responsive, operating means for operating the pump means only once each time a vacuum is supplied to the operating means; conduit means leading from the outlet of the pump means to the carrier for conveying a fluid pumped by the pump means to the carrier; the valve comprising a three-way control valve, one port of which is connected to the vacuum source, one port of which is connected to the holding means and the third port of which is connected to the operating means; the control means being connected to the valve so as to actuate the valve so that a vacuum is not supplied to the holding means and is supplied to the operating means each time the carrier is in the other location.

BRIEF DESCRIPTION OF THE DRAWING

The invention is best more fully described with reference to the accompanying drawing in which:

The FIGURE shows in diagrammatic form a presently preferred embodiment or form of an apparatus in accordance with this invention.

The particular apparatus indicated is constructed so as to utilize the operative concepts or principles set forth and defined in the appended claims forming a part of this disclosure. It will be realized that these concepts or principles can be utilized in a diverse variety of ways and manners through the use or exercise of routine engineering skill.

DETAILED DESCRIPTION

In the drawing there is shown an apparatus 10 in accordance with this invention. This apparatus 10 forms a part of a larger apparatus, such as a testing device as set forth and claimed in the Phillips U.S. Pat. No. 3,430,415, issued Mar. 4, 1969, entitled "TESTING DEVICE". In the interest of brevity only those parts of a testing device as shown in this Phillips patent as are important or significant to the present invention are indicated in the drawing and described in this specification. It is considered that anyone with reasonable engineering skill in the field of automated testing equipment should be able to easily incorporate an apparatus 10 in accordance with this invention in a testing device as shown in this Phillips patent or within other reasonably related differently constructed or differently operated testing devices.

The apparatus 10 includes a carrier 12 which may conveniently be mounted to two elongated rods 14 so as to be capable of being moved in a linear path from a first location toward the left of the FIGURE of the drawing where this carrier 12 is shown in full lines to a second location toward the right of the FIGURE of the drawing where this carrier 12 is shown in dotted lines. It is to be understood that these first and second locations may be varied as required during the use of the complete testing apparatus. Thus the second location may be varied each time the carrier 12 is traversed between the two locations noted so that the carrier may be positioned over successive of a series of test tubes 16 or the like.

In the apparatus 10 only one of the rods 14 is illustrated and the other of these rods 14 is immediately in back of the illustrated rod 14. These rods pass through correspondingly shaped openings (not shown) in the carrier 12 serving as bearings. It is not considered necessary to show this type of structure in detail in the drawing since it constitutes a well known track-type structure.

The carrier 12 may be reciprocated between locations as noted along the rods 14 in a variety of different conventional ways. One manner of causing movement is through the use of a hydraulic cylinder 18 having a piston rod 20 extending from the cylinder 18. This piston rod 20 is connected directly to the carrier 12 so that as the cylinder 18 is used the rod 20 moves the carrier 12 between the two positions as noted.

The cylinder 18 may be controlled so as to obtain reversal of the carrier 12 in a wide variety of different electrical mechanical, electro-mechanical manners. For the sake of simplicity of description the apparatus 10 is shown as including a hydraulic control valve 22 mounted directly upon the carrier 12 so that an actuator 24 extends outwardly from opposed sides 26 of the carrier 12. This valve 22 is connected by a flexible line 28 to a conventional source of hydraulic fluid under pressure and is connected to the cylinder 18 by two other lines 30 and is also connected to a flexible return line 32.

This arrangement is essentially a conventional arrangement enabling the cylinder 18 to be reversed whenever the actuator 24 comes in contact with either of two different stops 34 which are used in the apparatus 10. These stops 34 may of course be made so that either or both of their positions may be manually or automatically adjusted or varied as desired.

The carrier 12 also holds a vacuum distribution valve 36 which is provided with a valve actuator 38 extending from both of the sides 26. This distribution valve 36 is connected by a flexible line 40 to a conventional vacuum source such as a vacuum pump 42. It is also connected by an internal passage 44 to a tubular holder 46 mounted on the carrier 12. This holder 46 may be either rigidly mounted on the carrier 12 or may be movably mounted on this carrier 12 if this is desired. It is provided with an end 48 which is adapted to be utilized in supporting a small disk 50 such as, for example, a disk of absorbent paper when the carrier 12 is moved from the position in which it is illustrated in dotted lines toward the right of the FIGURE of the drawing.

The disk 50 is capable of being held in place against the end 48 by means of a vacuum produced by the pump 42. Preferably this disk 50 is of such a character that when this vacuum is discontinued it is capable of falling off of the end 48. The carrier 12 is constructed so that when this carrier 12 moves to the second position indicated by dotted lines in the drawing the actuator 38 will engage the stop 34 adjacent to this position so as to manipulate or actuate the valve 36 in such a manner that the vacuum applied to the tubular holder 46 is cut off or discontinued. When this occurs the disk 50 will normally be released so as to fall downwardly into an appropriate receptacle 51 located adjacent to the second position noted.

If desired the valve 36 may be constructed so as to vent atmospheric pressure into the interior of the holder 46 so as to "break" any vacuum within the interior of this holder 46 which might tend to hold the disk 50 against the end 48 even after a vacuum is no longer supplied as a result of actuation of the valve 36. In many instances, however, the mere cutting off or breaking of the vacuum being supplied to the tubular holder 46 will be adequate to cause release of the disk 50 because of leakage between the disk 50 and the end 48.

When this occurs the valve 36 will be actuated so that this vacuum will be applied through another flexible line 52 to the interior of a cylinder 54 mounted upon and in effect forming a part of a pump mechanism 56. As the vacuum is supplied to the interior of the cylinder 54 it will draw a piston 58 in the cylinder 54 against the spring 60 so as to actuate the pump mechanism 56. As this occurs the pump mechanism 56 will pump a fluid from a container 61 through another flexible line 62 to a distribution nozzle 64 mounted on the carrier 12 so as to terminate adjacent to the end 48.

This will serve to eject a quantity of fluid through the nozzle 64 as determined by the pump mechanism 56. Preferably this pump mechanism 56 is constructed so that each time it is actuated identical quantities of fluid will be moved by it. With the apparatus 10 the fluid pumped by the pump mechanism 56 will move downwardly from the nozzle 64 into the receptable 51. Preferably this nozzle 64 is located so as to be adjacent to and directly against the exterior of the tubular holder 46 a short distance above the end 48. When the nozzle 64 is located in this manner fluid emitted through it will to a degree tend to "adhere" to the exterior of the tubular holder 46 as it moves downwardly as a result of surface tension phenomena or considerations.

Such downwardly moving fluid will of course be directed by the end 48 so as to fall off of this end 48 in the same path as the disk 50. This provides an effective means of locating or positioning the fluid relative to the disk 50. Further, if for any reason the disk 50 should tend to adhere to the end 48 after a vacuum is no longer supplied to the interior of the tubular holder 46 the weight of the downwardly moving fluid at the end 48 will aid in displacing the disk 50 from the end 48.

After this occurs the engagement of a stop 34 toward the right of the drawing with the actuator 24 will next cause a reversal of the carrier 12 so that it moves back to the position toward the left of the FIGURE of the drawing where this actuator 24 is again engaged by the other stop 34. At this point the actuator 38 will also be engaged with the stop 34 toward the left of the FIGURE of the drawing so as to actuate the valve 36 so that the holder 46 may lift and support an object such as the disk 50 so that this disk 50 will be moved as the carrier 12 is moved from what was referred to in the preceding as the first position to the second position. Concurrently this will release the vacuum in the cylinder 54 allowing the spring 60 to return the piston 58 to its initial position. Also concurrently engagement of the actuator 24 with the stop 34 will cause movement of the carrier 12 from this first position to the second position.

I claim:

1. In a testing apparatus which includes a carrier for use in transporting a specimen from a first location to another location, means for moving said carrier from said first location to said other location and back to said first location, a vacuum source, a vacuum holding means for holding a specimen on said carrier through the use of a vacuum, a line connecting said vacuum source to said holding means, said line including a valve, and control means for operating said valve so that a vacuum is supplied to said holding means when said carrier is in said first location and as said carrier is moved to said other location and is not supplied to said holding means as said carrier is moved from said other location back to said first location in which the improvement comprises:

a pump means for pumping a predetermined quantity of a solution each time said pump means is actuated, vacuum responsive operating means for operating said pump means only once each time a vacuum is supplied to said operating means, conduit means leading from the outlet of said pump means to said carrier for conveying a fluid pump by said pump means to said carrier, said valve comprising a three-way control valve, one port of which is connected to said vacuum source, one port of which is connected to said holding means, and another port of which is connected to said operating means, said control means being connected to said valve so as to actuate said valve so that a vacuum is no longer supplied to said holding means and is supplied to said operating means each time said carrier is in said other location.

* * * * *